United States Patent
Kanazawa et al.

(10) Patent No.: US 10,416,136 B2
(45) Date of Patent: Sep. 17, 2019

(54) CONTROLLING APPARATUS

(71) Applicant: SHIMADZU CORPORATION, Kyoto-shi, Kyoto (JP)

(72) Inventors: Shinji Kanazawa, Kyoto (JP); Fuyuki Okamoto, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 147 days.

(21) Appl. No.: 15/321,476

(22) PCT Filed: Jun. 24, 2014

(86) PCT No.: PCT/JP2014/066647
§ 371 (c)(1),
(2) Date: Dec. 22, 2016

(87) PCT Pub. No.: WO2015/198389
PCT Pub. Date: Dec. 30, 2015

(65) Prior Publication Data
US 2017/0146500 A1 May 25, 2017

(51) Int. Cl.
G01N 30/88 (2006.01)
G01N 35/00 (2006.01)
G01N 30/02 (2006.01)

(52) U.S. Cl.
CPC ........... G01N 30/88 (2013.01); G01N 35/00 (2013.01); G01N 35/0092 (2013.01);
(Continued)

(58) Field of Classification Search
None
See application file for complete search history.

(56) References Cited

U.S. PATENT DOCUMENTS

| 5,139,744 A * | 8/1992 | Kowalski | G01N 21/253 422/63 |
| 2005/0036913 A1* | 2/2005 | Yamakawa | G01N 35/00594 422/65 |
| 2010/0300217 A1* | 12/2010 | Mizumoto | G01N 15/14 73/863.01 |

FOREIGN PATENT DOCUMENTS

| CN | 101900720 A | 12/2010 |
| EP | 2 256 476 A2 | 12/2010 |

(Continued)

OTHER PUBLICATIONS

Communication dated May 31, 2017 from the European Patent Office in counterpart application No. 14896137.8.

(Continued)

Primary Examiner — Paul M. West
Assistant Examiner — Mark A Shabman
(74) Attorney, Agent, or Firm — Sughrue Mion, PLLC

(57) ABSTRACT

A controlling apparatus 110 to control an operation of an analyzing apparatus 1 and make the analyzing apparatus 1 execute a predetermined analysis, the controlling apparatus 110 including: a communicating module 60 that maintains reception of electricity when the analyzing apparatus 1 is in a power-on state, and is capable of receiving a control signal from an external apparatus 2 at all times; and a unit power controlling section 23 for acquiring the control signal through the communicating module 60, stopping electricity supply to a unit 31, 321, 322, 323 and/or 324 of the analyzing apparatus 1 at a first timing based on the control signal, and restarting the electricity supply to the unit 31, 321, 322, 323 and/or 324 at a second timing based on the control signal, so as to effectively suppress the electricity consumption when the analysis is not executed and facilitate the restart of the analysis.

7 Claims, 5 Drawing Sheets

(52) U.S. Cl.
CPC .. *G01N 35/00871* (2013.01); *G01N 2030/027* (2013.01); *G01N 2030/8804* (2013.01)

(56) References Cited

FOREIGN PATENT DOCUMENTS

| | | |
|---|---|---|
| JP | 06160397 A | 6/1994 |
| JP | 2003-121449 A | 4/2003 |
| JP | 2011-13112 A | 1/2011 |
| JP | 2012-255663 A | 12/2012 |

OTHER PUBLICATIONS

Written Opinion for PCT/JP2014/066647 dated Sep. 30, 2014. [PCT/ISA/237].
"Catalog for GCMS-QP2010 SE", Shimadzu Corporation, May 17, 2010.
"Operating Manual for GCMS-QP2010 SE", Shimadzu Corporation, May 17, 2010, p. 25-27.
International Search Report for PCT/JP2014/066647 dated Sep. 30, 2014.
Communication dated Sep. 29, 2017 from the State Intellectual Property Office of the P.R.C. in counterpart Chinese application No. 201480080111.6.
Communication dated Oct. 10, 2017 from the Japanese Patent Office in counterpart Japanese application No. 2016-528781.

\* cited by examiner

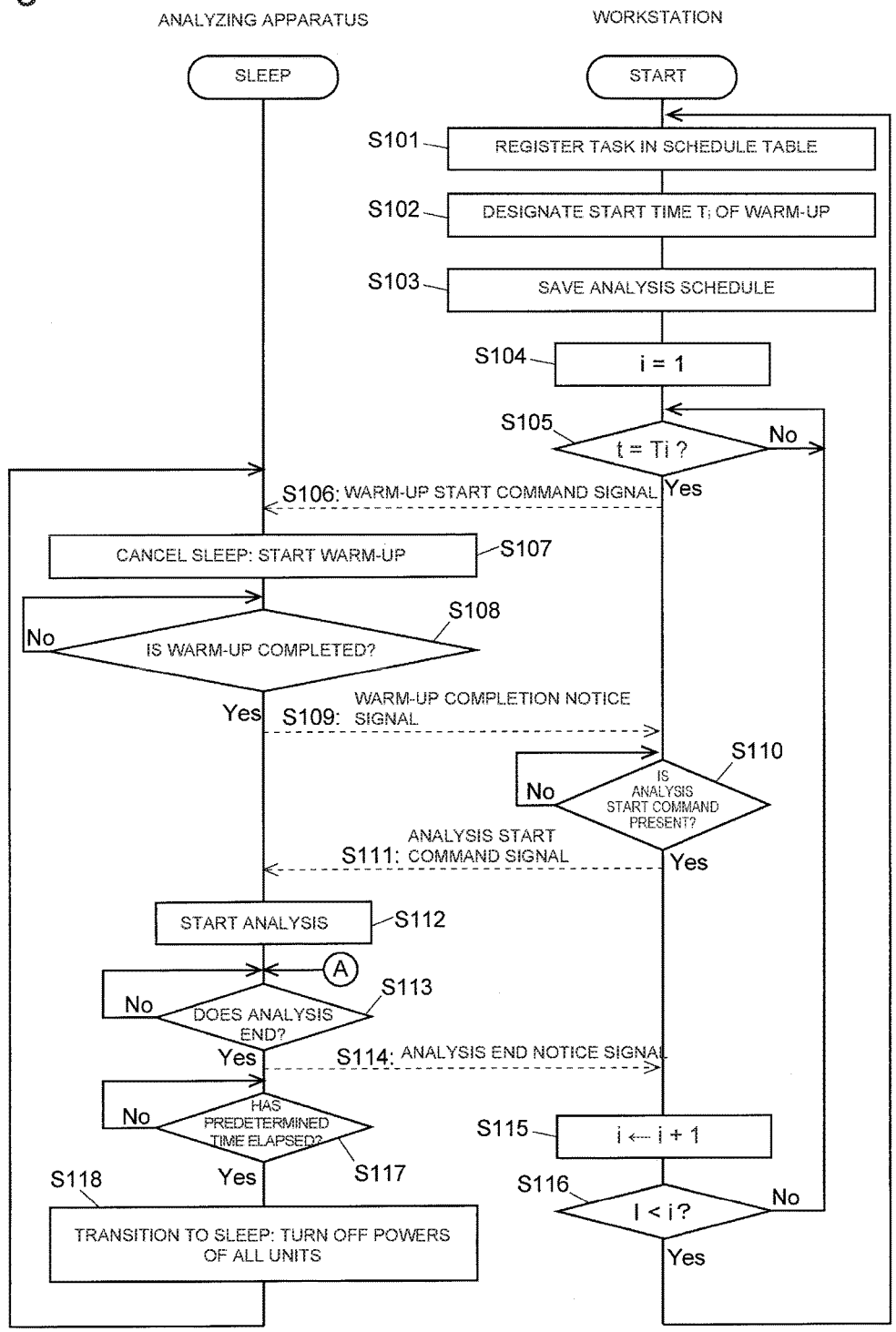

CONTROLLING APPARATUS

CROSS REFERENCE TO RELATED APPLICATIONS

This application is a National Stage of International Application No. PCT/JP2014/066647 filed Jun. 24, 2014, the contents of all of which are incorporated herein by reference in their entirety.

TECHNICAL FIELD

The present invention relates to a controlling apparatus for an analyzing apparatus that controls the operation of the analyzing apparatus and makes the analyzing apparatus execute a predetermined analysis.

BACKGROUND ART

An analyzing apparatus for executing a predetermined analysis for a sample and obtaining information about the components or structure of the sample is used in various fields such as drug/food development, medical care, environment research and basic study.

Typically, such an analyzing apparatus is configured to include a plurality of units as functional units that respectively perform a plurality of steps constituting a sequence of analysis work. As an example, a liquid chromatograph (LC) includes a liquid sending pump for sending a liquid mobile phase to a mobile phase passage, an injector for injecting a sample into the mobile phase passage, a column oven for performing the temperature control of a column for separating components contained in the sample, a detector for detecting separated components flowing through the mobile phase passage on the downstream side of the column, and other components. Generally, commercially available analyzing apparatuses further include communication device for performing the communication with a controlling computer (a PC, workstation or the like) that externally controls the operation of the analyzing apparatus, and the controlling computer and the analyzing apparatus constitute an analyzing system. Recently, an analyzing apparatus equipped with programs (an Operating System, application software and the like) and thereby constituting an analyzing system by itself has been provided.

As an example of such analyzing systems, an analyzing system having a start function to put the analyzing apparatus into an operating state, an analysis execution function to make the analyzing apparatus execute the analysis, a pause function to put the analyzing apparatus into a waiting state, and a schedule management function to register these functions in a schedule table as tasks and to sequentially execute the registered tasks has been provided. In such a schedule table, generally, not only the analysis condition but also the execution timing of each task are managed based on the designation by a user, and thereby, the user can start the analysis at a desired timing. The "timing" mentioned here includes a previously designated time, a time point when a predetermined time has elapsed since a certain time point (for example, the end time of a particular task), and the like.

The "operating state" of the analyzing apparatus means a state where one or a plurality of units of the analyzing apparatus are performing predetermined operations relevant to the execution of the analysis or the preparation (warm-up), and the "waiting state" means a state where no units are performing the above predetermined operations. For example, when the liquid sending pump of the LC is sending liquid, the LC is in the operating state as a whole, even if the other units have paused the above predetermined operations. When the LC is in the waiting state, all units including the pump have stopped the above predetermined operations. Here, even in the waiting state, the electricity supply to the units is maintained, and the units perform the switching of the above operations in the power-on state.

CITATION LIST

Non Patent Literature

[Non Patent Literature 1] "Catalog for GCMS-QP2010 SE", SHIMADZU CORPORATION, May 17, 2010

[Non Patent Literature 2] "Operating Manual for GCMS-QP2010 SE", SHIMADZU CORPORATION, May 17, 2010, p. 25-27

SUMMARY OF INVENTION

Technical Problem

Typically, a warm-up operation necessary before the start of the analysis requires time (for example, in the case of the LC, it takes about 60 to 90 minutes to stabilize a light source). Therefore, in the analyzing system having the above-described functions, the user often designates the start time of the warm-up operation at the time of the registration of the task in the schedule table, for starting the analysis just at a planned time. In order to start the warm-up operation at the designated time, the power of the analyzing apparatus needs to be in the on-state, at least by the designated time. However, while the start of the operation is preset in advance of a designated time, turning on the power of the analyzing apparatus shortly before the designated time makes no sense, considering the purpose of the preset. Accordingly, it is often the case that, when the task with the designation of the execution time is registered in the schedule table, the power of the analyzing apparatus is turned on and kept in the on-state until the designated time. In this period, a certain amount of electricity is consumed. Further, even while the above pause function puts the analyzing apparatus into the waiting state after the analysis ends, the electricity supply to the units is maintained. This also causes the increase in electricity consumption.

Hence, as a configuration for suppressing the electricity consumption when the analyzing apparatus is not used, for example, an analyzing system previously provided by the applicant has an electricity saving mode of selectively stopping the operation of a designated unit (see Non Patent Literature 1). For example, the power to the heater of a column oven is turned off in a gas chromatograph mass spectrometer (GC-MS). Generally, in the GC-MS, it takes about three hours until a mass spectrometry section (MS section) becomes stable in a high vacuum state after the activation of the apparatus. If the power is entirely turned off after an analysis ends, the user has to wait a long time after turning on the apparatus and before starting the next analysis, and therefore, which is inconvenient in routine use. The above electricity saving mode is provided in view of such a circumstance, where only a unit maintaining the vacuum environment is operated, and the powers to the other units are turned off. Thereby, the reduction in electricity consumption is achieved.

However, in the above-described analyzing system, in order to restart the analysis after the temporary transition to the electricity saving mode, the user needs to manually cancel the electricity saving mode, and when an automatic restart of the analysis is preferred, the manual cancel causes the user to have a troublesome feeling.

The present invention has been made in view of the above circumstances, and an object of the present invention is to provide an analyzing apparatus that effectively suppresses the electricity consumption when the analysis is not executed and that facilitates the restart of the analysis.

Solution to Problem

The present invention, which has been made for solving the above problem, is a controlling apparatus for an analyzing apparatus, the controlling apparatus controlling an operation of the analyzing apparatus and making the analyzing apparatus execute a predetermined analysis, the controlling apparatus including:
a) a communicating module that maintains reception of electricity when the analyzing apparatus is in a power-on state, and is capable of receiving a control signal from an external apparatus at all times; and
b) unit power controlling means for acquiring the control signal through the communicating module, stopping electricity supply to a unit of the analyzing apparatus at a first timing based on the control signal, and restarting the electricity supply to the unit at a second timing based on the control signal.

The "unit" in the present invention means a functional unit that performs each of a plurality of steps constituting a sequence of analysis work. In the case of an LC, for example, it is a liquid sending pump, an injector, a column oven, a detector or the like. It may further include an automatic sampler for collecting a liquid sample to be introduced into the LC. The unit power controlling means is means for integrally controlling the unit or units in the present invention, and is different from the unit or units in the present invention that perform predetermined steps proper to the analysis work.

Examples of the above "first timing" include a time point when the communicating module receives the control signal from the external apparatus, a time designated in advance by a user, the time of the completion of an analysis, a time point when a predetermined time has elapsed with no operation, and the like. Examples of the above "second timing" include a time designated in advance by the user, a time point when a predetermined time has elapsed after the completion of the preceding analysis, and the like.

The "controlling apparatus" in the present invention includes a controlling instrument (for example, a system controller of the LC) that is provided integrally with the analyzing apparatus, a controlling computer that is provided separately from the analyzing apparatus and that externally controls the analyzing apparatus, and the like.

According to the above configuration, the controlling apparatus can receive a control signal from the external apparatus through the communicating module, at all times, when the analyzing apparatus is in the power-on state, and the unit power controlling means stops the electricity supply to a unit of the analyzing apparatus, at the first timing based on the control signal that the communicating module receives from the above external apparatus. Thereby, the electricity consumption by the unit becomes zero. Therefore, for example, by adopting, as the above first timing, the time of the completion of the analysis scheduled in the above external apparatus or the like as described above, the electricity consumption when the analysis is not executed is suppressed. Furthermore, the unit power controlling means restarts the electricity supply to the above unit, at the second timing based on the control signal that the communicating module receives from the above external apparatus. That is, for example, when the user designates a time in advance through the above external apparatus, electricity is automatically supplied to the above unit at the designated time, and therefore, the user's manual operation for restarting the electricity supply to each unit is unnecessary, allowing for an easy restart of the analysis. Specifically, when the user presets, on the above external apparatus, the start of an analysis planned to be executed after several hours, or the start of a warm-up operation in the preparatory stage of the analysis, a time shortly before the start is adopted as the above second timing, and thereby, the automation of the analysis restart can be achieved with the suppression of the electricity consumption when the analysis is not executed.

Furthermore, the communicating module can receive the control signal from the external apparatus at all times and therefore receives predetermined control signals even during the interruption of the electricity supply to all units of the analyzing apparatus, and the unit power controlling means can perform the stop and restart of the electricity supply to the units, at the timings based on the control signals.

The unit power controlling means may be configured to stop the electricity supply to all of a plurality of units included in the analyzing apparatus at the first timing, and restart the electricity supply to all of the plurality of units at the second timing.

With this configuration, the electricity consumption by all units becomes zero, which further contributes to the reduction in the electricity consumption when the analysis is not executed.

Preferably, the second timing should be a time point when the communicating module receives a control signal for commanding a start of analysis work registered in an analysis schedule that is managed by the controlling apparatus or the external apparatus.

Here, the "start of the analysis work" means the start of the execution of the analysis or the warm-up operation.

According to the above configuration, when the external apparatus commands the controlling apparatus to start the analysis work, this triggers restart of the electricity supply to the units, and the units execute the operations proper to the analysis work in accordance with the command. That is, the analysis work is started simultaneously with the restart of the electricity supply, and therefore, a further efficient electricity saving is realized. This configuration is particularly useful in the case where the user intermittently executes a plurality of analyses at desired timings.

Advantageous Effects of Invention

The analyzing apparatus according to the present invention can effectively suppress the electricity consumption when the analysis is not executed, and can facilitate the restart of the analysis.

BRIEF DESCRIPTION OF DRAWINGS

FIG. 4 is a flowchart showing an example of the flow of a process performed by the analyzing apparatus and a workstation when the sample analyzing system shown in FIG. 1 performs analysis work.

DESCRIPTION OF EMBODIMENTS

Hereinafter, an embodiment for implementing the present invention will be described in detail with reference to the drawings. In the following description, identical numerals are assigned to members having identical functions to those in previously described drawings, and the descriptions thereof are omitted.

Figure 1:
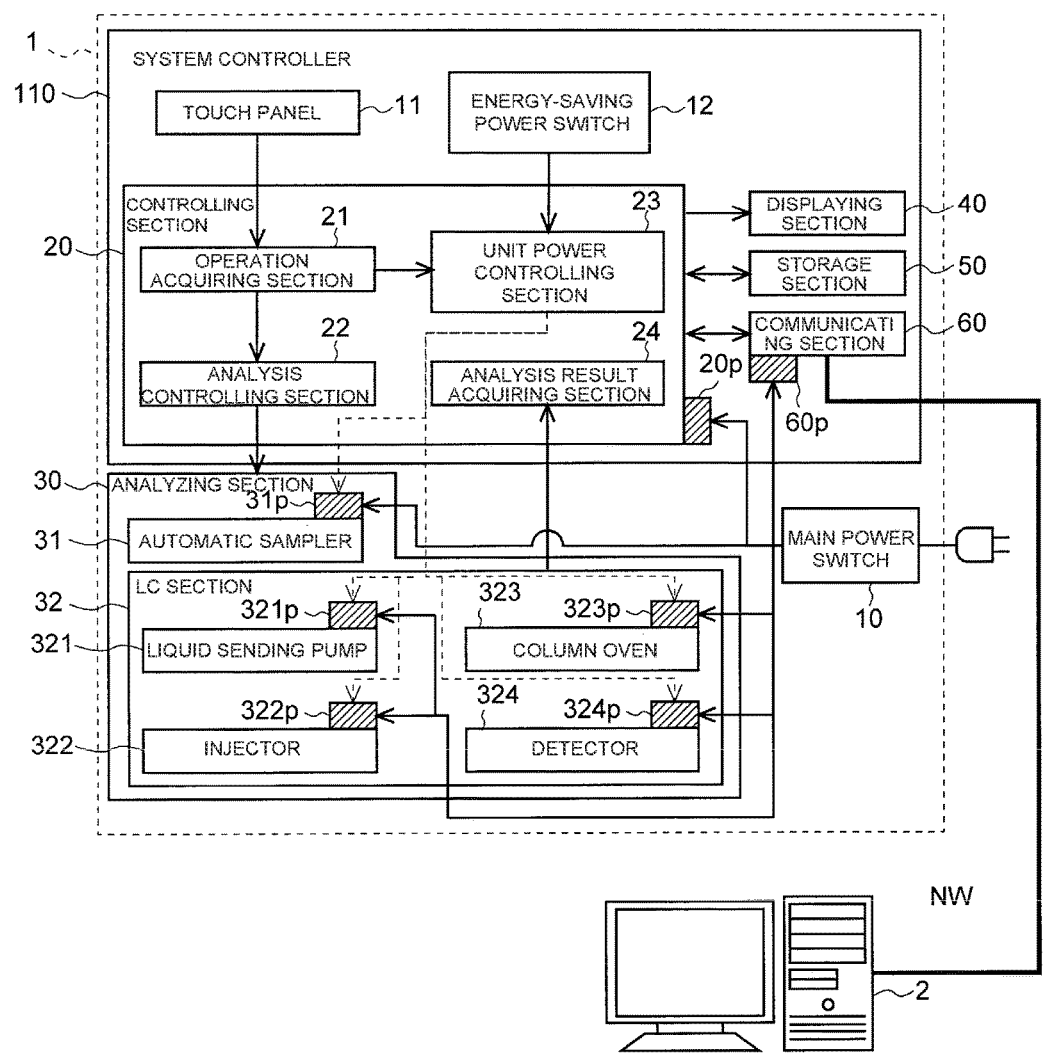
FIG. 1 is a block diagram showing a schematic configuration of a sample analyzing system including an analyzing apparatus according to an embodiment of the present invention.

FIG. 1 is a block diagram showing a schematic configuration of a sample analyzing system including an analyzing apparatus according to an embodiment of the present invention. The sample analyzing system according to the embodiment includes an analyzing apparatus 1, and a workstation 2 (corresponding to an external apparatus in the present invention) connected to the analyzing apparatus 1, which manages analysis work performed by the analyzing apparatus 1 and analyzes and processes data obtained in the analyzing apparatus 1.

Configuration of Analyzing Apparatus 1

In the embodiment, the analyzing apparatus 1 is a liquid chromatograph (LC). However, the actual form of the analyzing apparatus 1 is not limited to this, and may be a liquid chromatograph mass spectrometer (LC-MS), a gas chromatograph (GC), a gas chromatograph mass spectrometer (GC-MS), a spectrophotometer, or the like. The analyzing apparatus 1 may be another laboratory instrument or medical instrument, and a measurement method and an object is not limited as long as an analyzing apparatus can be controlled by the external apparatus and includes a configuration corresponding to units in the present invention.

As shown in FIG. 1, the analyzing apparatus 1 is configured to include a main power switch 10, a system controller 110 (corresponding to a controlling apparatus in the present invention), and an analyzing section 30.

The main power switch 10 is a mechanical switch for switching ON/OFF of a main power for the whole of the analyzing apparatus 1, and is implemented, for example, as a locker switch, a push-button switch or the like. When a user operates the main power switch 10 while the analyzing apparatus 1 is in a main-power-on state, the analyzing apparatus 1 is forcibly put into a main-power-off state regardless of the currently performing operation. A conceivable situation where the main power switch 10 is operated in the middle of the analysis work is a case where the maintenance is urgently needed, or other cases.

When the analyzing apparatus 1 is put into the main-power-on state by the operation to the main power switch 10, electricity is supplied to power circuits of the units of the analyzing apparatus 1 (for example, a controlling-section power 20p, a communicating-section power 60p, and unit powers 31p, 321p, 322p, 323p and 324p, which are described later).

The system controller 110 controls the operations of the units of the analyzing section 30, based on control signals transmitted from the workstation 2. The system controller 110 includes a touch panel 11, an energy-saving power switch 12, a controlling section 20, a displaying section 40, a storage section 50 and a communicating section 60 (corresponding to a communicating module in the present invention).

The touch panel 11 is means for detecting a touch by the user (the contact or approach of a commanding subject), and is implemented, for example, as a capacitive type or resistive membrane type touch panel. In the embodiment, the input of an analysis condition and an execution command for analysis can be performed also by an input operation through the touch panel 11, but predetermined analysis is generally executed based on the control signal received from the workstation 2 through the communicating section 60.

The energy-saving power switch 12 is a switch controlled by software, and when the user presses the energy-saving power switch 12, a pressing signal is output to the controlling section 20. Pressing the energy-saving power switch 12 triggers transition to a sleep state and cancellation of the sleep state of the analyzing apparatus 1, which is later described.

Figure 2:
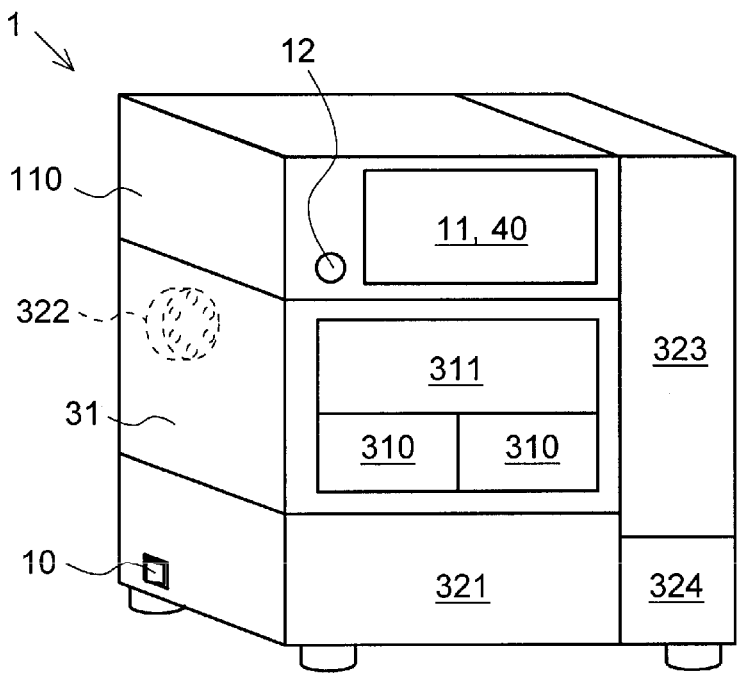
FIG. 2 is a perspective diagram showing an overview of the analyzing apparatus shown in FIG. 1.

FIG. 2 shows an overview of the analyzing apparatus 1. As shown in FIG. 2, the analyzing apparatus 1 is an integrated apparatus configured by combining a plurality of units (an automatic sampler 31, a liquid sending pump 321, an injector 322, a column oven 323 and a detector 324) constituting the analyzing section with the system controller 110 including the controlling section 20 for controlling the operations of them. The system controller 110 incorporates the storage section 50 and the communicating section 60 in addition to the controlling section 20, and includes the touch panel 11, the energy-saving power switch 12 and the displaying section 40, on the front side of the analyzing apparatus 1. The touch panel 11 is provided integrally with the displaying section 40.

The main power switch 10 is provided on a lateral side or back side of an outer housing of the analyzing apparatus 1. In FIG. 2, the main power switch 10 is provided on a lateral side of an outer housing of the liquid sending pump 321, but of course, may be provided on another unit or the system controller 110. Further, each unit may include an individual power switch button.

Refer to FIG. 1 again. Here, the description of the system controller 110 is temporarily suspended, and the analyzing section 30 first will be described.

The analyzing section 30 executes a predetermined analysis, in accordance with control by the system controller 110 (particularly, the controlling section 20). The analyzing section 30 includes the automatic sampler 31 and the LC section 32.

The automatic sampler 31 collects a sample analyzed in the LC section 32, and includes a sampling needle for sucking the sample from each sample container set on one or a plurality of sample racks 310 (see FIG. 2). A check window 311 is provided on an upper portion of which the sample rack 310 is housed, and through this window, the user can visually check the set position of the sample container and the lowered position of the needle.

The automatic sampler 31 further comprises a sample cooler for keeping the temperature of the sample constant and a needle driving mechanism for moving the needle in the horizontal direction and the vertical direction (both are not illustrated), as electricity consuming sections in the unit.

Next, the units of the LC section 32 will be described. The LC section 32 includes, as the units, a liquid sending pump 321 for sending a mobile phase contained to a mobile phase container not illustrated, an injector 322 for injecting the liquid sample into a mobile phase passage, a column oven 323 for housing a column not illustrated and maintaining the column at a predetermined temperature, and a detector 324 for detecting sample components sequentially eluted from the column.

Some examples of electricity consuming sections of the units are shown as follows. The liquid sending pump 321 and the injector 322 include driving mechanisms for operating a plunger and a valve. The column oven 323 includes a heater for keeping the above column at a constant temperature (the heater does not always heat the column, and sometimes cools it). In the case where the detector 324 is a PDA (Photodiode Array) detector, the detector 324 includes a deuterium lamp or a tungsten lamp as a light source and a PDA as a sensor.

Here, the automatic sampler 31, the liquid sending pump 321, the injector 322, the column oven 323 and the detector 324 include the unit power 31$p$, 321$p$, 322$p$, 323$p$ and 324$p$, respectively for adequately supplying electricity to the electricity consuming sections in the units. They are controlled by a unit power controlling section 23 described later, in addition to the main power switch 10.

In FIG. 2, the injector 322 is illustrated in such a manner as to be housed in the automatic sampler 31. However, the arrangement of the injector 322 is not limited to this, and for example, the injector 322 may be housed in the column oven 323. As can be seen from this example, the units only have to be functional units that respectively perform a plurality of steps proper to the analysis work, and do not need to be provided as separate instruments. Needless to say, the arrangement of the units is not limited to the specific form shown in FIG. 2.

With reference to FIG. 1 again, the description of the system controller 110 is restarted.

The displaying section 40 displays information used by the analyzing apparatus 1, and is implemented, for example, as a displaying device such as a LCD (Liquid Crystal Display). The displaying section 40 is provided on the back side of the touch panel 11 so as to overlap with the touch panel 11 (see FIG. 2), and assists the user's touch operation on the touch panel 11 by displaying GUI (Graphical User Interface) buttons and the like.

The storage section 50 non-transitorily stores a controlling program and an OS (Operating System) program that the controlling section 20 of the analyzing apparatus 1 executes, an application program by which the controlling section 20 executes a variety of functions as the analyzing apparatus in the present invention, and a variety of data that the controlling section 20 reads when executing the application program, and is implemented as a non-volatile storage device such as a ROM (Read Only Memory), a flash memory, an EPROM (Erasable Programmable ROM), an EEPROM (Registered) (Electrically EPROM), an HDD (Hard Disk Drive) and an SSD (Solid State Drive).

The communicating section 60 is means for performing the connection with an external apparatus and the like, and establishes the connection between the analyzing apparatus 1 and the workstation 2 through a network cable NW (or a wireless LAN (Local Area Network)). The communicating section 60 includes the communicating-section power 60$p$ as a power circuit in the module. While the analyzing apparatus 1 is in the main-power-on state, the communicating-section power 60$p$ is in the on-state at all times, and the electricity supply to the communicating section 60 is maintained. Thereby, the analyzing apparatus 1 can receive the command from the workstation 2 even during the sleep state described later.

The controlling section 20 manages the functions of the elements of the analyzing apparatus 1, and controls the operation of the analyzing apparatus 1. The controlling section 20 is implemented, for example, as a CPU (Central Processing Unit) or the like, and the later-described elements of the controlling section 20 functions when the CPU as the controlling section 20 reads the program stored in the storage section 50, in a non-illustrated memory constituted by a volatile storage device such as a RAM and executes the program.

As shown in FIG. 1, the controlling section 20 includes, as functional blocks, an operation acquiring section 21, an analysis controlling section 22, the unit power controlling section 23 and an analysis result acquiring section 24.

The operation acquiring section 21 acquires an operation signal detected by the touch panel 11 (for example, the capacity value of each electrode in the case of a capacitive type touch panel), specifies coordinates of a position on which the user has performed a touch operation, based on the operation signal, and outputs the coordinates, as operation information, to the analysis controlling section 22 and unit power controlling section 23 described later. Known techniques can be employed for a method of specifying the coordinates.

The analysis controlling section 22 controls the operations of the automatic sampler 31 and the LC section 32, such that the analysis commanded by the user is appropriately executed. Specifically, the analysis controlling section 22 acquires an analysis condition and the like set on the workstation 2, through the communicating section 60, and outputs a predetermined driving signal to the automatic sampler 31 and the LC section 32, in accordance with the acquired analysis condition and the like. Furthermore, since the analyzing apparatus 1 includes the touch panel 11, the analysis controlling section 22 may determine an analysis condition and the like, based on the operation information acquired from the operation acquiring section 21, and may output a predetermined driving signal to the automatic sampler 31 and the LC section 32, in accordance with the determined analysis condition and the like. In addition, the analysis controlling section 22 may display the currently set analysis condition and the like, as an image, on a screen of the displaying section 40.

When a predetermined condition is satisfied, the unit power controlling section 23 stops the electricity supply to all units of the analyzing section 30. That is, the unit powers 31$p$, 321$p$, 322$p$, 323$p$ and 324$p$ of the units are all put into the off-state. The above predetermined condition is, for example, the detection of the pressing of the energy-saving power switch 12, the acquisition of the command from the workstation 2 for transitioning to the sleep state, or the arrival of timing set in advance (a time, a time point when the analysis is completed, or a time point when a predetermined time has elapsed with no operation).

In the specification, the state where the unit powers of all units are turned off in this way is referred to as the sleep state of the analyzing apparatus 1. Even in the sleep state, the electricity supply to the controlling section 20, the energy-saving power switch 12 and the like is maintained, and thereby, the unit power controlling section 23 can cancel the sleep state as described below.

Furthermore, the unit power controlling section 23 restarts the electricity supply to all units of the analyzing section 30, when a predetermined condition for canceling the sleep state is satisfied in the sleep state where the unit powers of all units are turned off. Specifically, the unit powers 31$p$, 321$p$, 322$p$, 323$p$ and 324$p$ of the units are all switched on. Thereby, the electricity consuming sections of the units can operate, and therefore, the user can restart the analysis work. The above predetermined condition is, for example, the detection of the pressing of the energy-saving power switch 12, the acquisition of the command from the workstation 2 for canceling the sleep state, the arrival of a time set in advance, or the like.

The "command from the workstation 2", which is one of the above-described examples, is not limited to an explicit command based on a user's manual input. For example, the termination and activation of an analysis controlling application program (hereinafter, referred to as an analysis controlling program) installed in the workstation 2 may be adopted as the command for transitioning to the sleep state and the command for canceling the sleep state, respectively. Further, the command for transitioning to the sleep state may be triggered by the detection of a state where no operation has been performed on the above analysis controlling program for a predetermined time, in a situation where the analyzing section 30 does not perform the analysis work.

Figure 3:
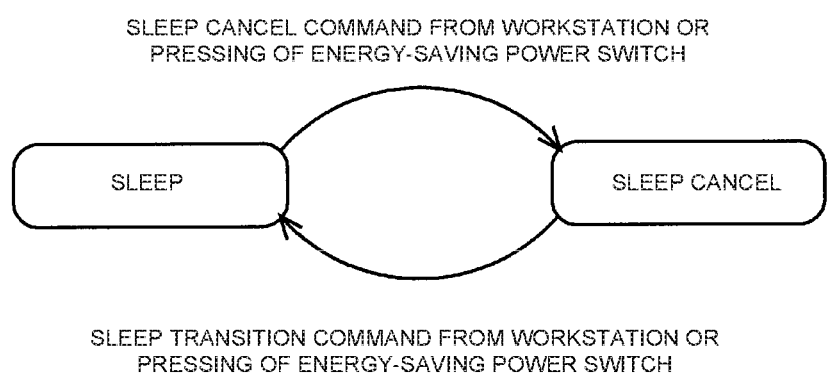
FIG. 3 is a state transition diagram showing transition between a sleep state and a sleep cancel state of the analyzing apparatus shown in FIG. 1.

FIG. 3 shows a transition form between the sleep state and the sleep cancel state of the analyzing apparatus 1. As described above, first, the analyzing apparatus 1 transitions between the sleep state and the sleep cancel state, by the pressing of the energy-saving power switch 12 by the user, which is a first trigger event. Furthermore, the analyzing apparatus 1 transitions between these two states, also by the command for transitioning to the sleep state or the command for canceling the sleep state from the workstation 2, which is a second trigger event. Additional trigger events include the arrivals of the above-described predetermined timings, but the illustration of them is omitted because of a variety of examples.

The description will be made with reference to FIG. 1 again. The analysis result acquiring section 24 acquires the analysis result obtained from the analysis by the LC section 32. The analysis result acquired by the analysis result acquiring section 24, in addition to the save in the storage section 50, may be displayed as an image on the screen of the displaying section 40, after the processing such as graph creation. Further, the analysis result is sent to the workstation 2 through the communicating section 60.

Similarly to the units of the analyzing section 30, the controlling section 20 includes the controlling-section power 20$p$. The controlling-section power 20$p$ is not controlled by the unit power controlling section 23, and ON/OFF is switched by the operation to the main power switch 10.

The touch panel 11, each of the energy-saving power switch 12, the displaying section 40 and the storage section 50 may be provided with a unique power circuit, but such a power circuit is omitted in FIG. 1 because of departing from the spirit of the present invention.

Processing Flow by Sample Analyzing System:
First Example

Next, a processing flow in the sample analyzing system constituted by the analyzing apparatus 1 and the workstation 2 will described with reference to FIG. 4, which is a flowchart, and FIG. 5A and FIG. 5B, which are screen display examples on a monitor attached to the workstation 2. It is assumed that the analyzing apparatus 1 is in the sleep state due to the above-described trigger event (see FIG. 3) and the user makes the analyzing apparatus 1 intermittently execute the analysis in order to measure the temporal change in a sample component at three-hour intervals.

First, the analysis controlling program installed in the workstation 2 registers a task in a schedule table (step S101). Here, as an example, the warm-up operation and the execution of the analysis are alternately registered as a plurality of tasks.

Figure 5A:
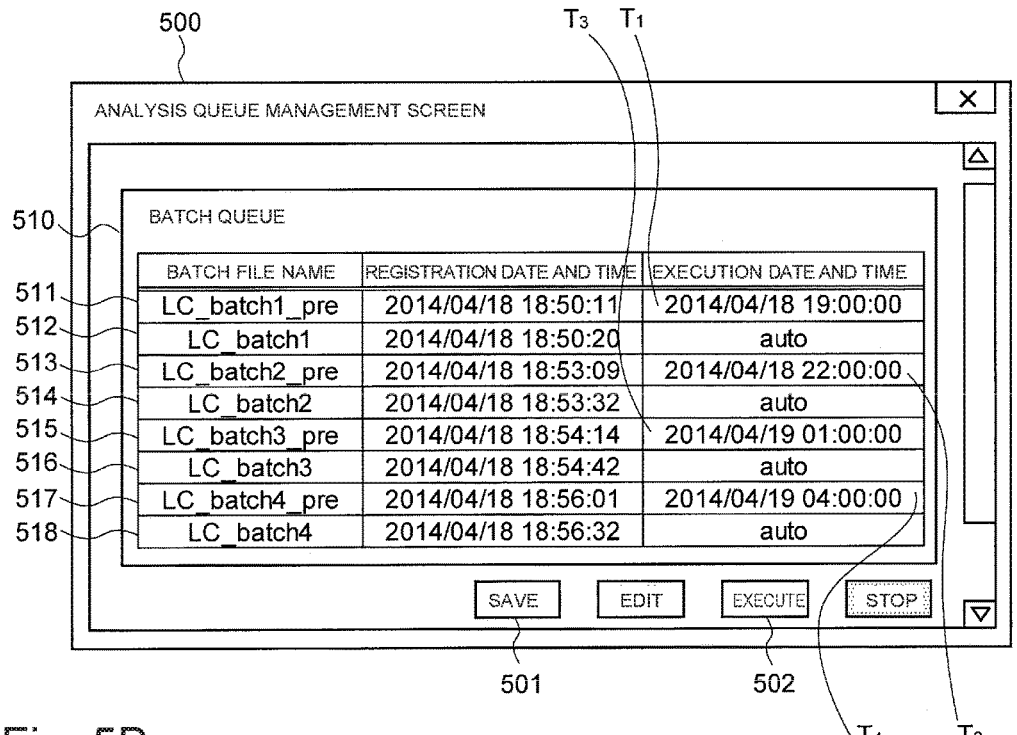
FIG. 5A and FIG. 5B are examples of the screen displayed by an analysis controlling program installed in the workstation of the sample analyzing system shown in FIG. 1.

Specifically, for example, the above analysis controlling program registers eight batch files 511 to 518 as tasks in a batch queue 510 (corresponding to an analysis schedule in the present invention) in order, in accordance with the user's input performed on an analysis queue management screen 500 shown in FIG. 5A.

In FIG. 5A, the batch files 512, 514, 516 and 518 are batch files for analysis execution, and the batch files 511, 513, 515 and 517 respectively preceding them are batch files for warm-up operation relevant to the subsequent analyses. The batch file for analysis execution includes a plurality of analyses that are specified by the combination of the position on the sample rack 310 of a sample collected by the sample needle, a sample type, an injection volume, an analysis method file and the like. The batch file for warm-up operation includes the sending of the mobile phase by the liquid sending pump 321, the stabilization of the light source, and the temperature control by the sample cooler of the automatic sampler 31 and the heater of the column oven 323 (the illustration of all is omitted in this document). As another example, the warm-up operation and the execution of the analysis may be combined into one batch file.

Furthermore, at this time, a start time $T_i$ ($1 \leq i \leq I$) of the warm-up operation relevant to each analysis is designated (step S102). In the batch files 511, 513, 515 and 517, the execution dates and times are registered, respectively, and the execution dates and times are $T_1$, $T_2$, $T_3$ and $T_4$. In the case where "auto" is input in the column "EXECUTION DATE AND TIME", the trigger of the execution is the completion of the work relevant to the preceding batch file. That is, the example shown in FIG. 5A is suitable for intermittent analyses in a night-time and unattended environment, because the analysis is automatically executed when the warm-up operation is completed.

When the task registration in the batch queue 510 and the designation of $T_i$ are completed as described above, the user clicks a save button 501 (in the case where the monitor attached to the workstation 2 includes a touch panel, the user taps on the commanding subject). Thereby, the above analysis controlling program saves the analysis schedule including them, in a storage area in the workstation 2 (step S103). Even when an execution button 502 is clicked instead of the save button 501, the analysis schedule is saved. By the click of the execution button 502, the executions of the batch files 511 to 518 are reserved.

First, for "LC_batch1_pre" (step S104), which is the first warm-up operation, whether the start time $T_1$ registered as the execution date and time coincides with the current time t is judged (step S105). In the case of not coinciding (No in S105), the analysis controlling program waits until the start time $T_1$.

In the case where the current time t coincides with $T_1$ (Yes in S105), the above analysis controlling program sends a warm-up start command signal to the communicating section 60 of the analyzing apparatus 1, through a non-illustrated communicating section of the workstation 2 (step S106).

Here, as shown in FIG. 4, the analyzing apparatus 1 is in the sleep state at the time point when the workstation 2 sends the warm-up start command signal. However, as described above, electricity is supplied to the communicating section 60 at all times as long as the main power of the analyzing apparatus 1 is ON, and therefore, the communicating section 60 can receive the signal sent in step S106.

When the communicating section 60 receives the warm-up start command signal from the workstation 2 as described above, the analyzing apparatus 1 cancels the sleep state, and starts the warm-up operation (step S107). Specifically, the unit power controlling section 23 switches on the unit powers 31p, 321p, 322p, 323p and 324p of the units of the analyzing section 30 described above, and restarts the electricity supply to the automatic sampler 31, the liquid sending pump 321, the injector 322, the column oven 323 and the detector 324. Then, the analysis controlling section 22 makes the analyzing section 30 execute the warm-up operation, in accordance with the batch file 511 (see FIG. 5A) included in the warm-up start command signal received by the communicating section 60 in step S106.

When the warm-up operation is completed (Yes in S108), the analysis controlling section 22 sends a warm-up completion notice signal to the workstation 2 through the communicating section 60 (step S109).

When the workstation 2 receives the warm-up completion notice signal, the above analysis controlling program judges whether the analysis start command is present (step S110). Here, as described above, in the case where the value of the column "EXECUTION DATE AND TIME" is "auto" in the batch queue 510, the execution trigger is the completion of the preceding work. Therefore, the above analysis controlling program judges that the next task "LC_batch1" is instantly executed, that is, judges that the analysis start command is present (Yes in S110), and sends an analysis start command signal to the communicating section 60 of the analyzing apparatus 1 (step S111).

When the communicating section 60 receives the analysis start command signal from the workstation 2, the analyzing apparatus 1 starts the analysis (step S112). Specifically, the analysis controlling section 22 makes the analyzing section 30 execute a predetermined analysis in accordance with the batch file 512 (see FIG. 5A) included in the analysis start command signal received by the communicating section 60 in step S111.

As described above, in the embodiment, the workstation 2 sends the analysis start command signal immediately after receiving the warm-up completion notice signal, and therefore, it is possible to shorten the period from the completion of the warm-up operation in the analyzing apparatus 1 (Yes in S108) to the analysis start in step S112, resulting in the suppression of extra electricity consumption after the completion of the warm-up.

When the analysis by the analyzing section 30 ends (Yes in S113), the analysis controlling section 22 sends an analysis end notice signal to the workstation 2 through the communicating section 60 (step S114). The analysis end notice signal may include the analysis result data that the analysis result acquiring section 24 acquires from the LC section 32.

When the workstation 2 receives the analysis end notice signal, the above analysis controlling program increments i (step S115), and waits for the start time $T_i$ of the next warm-up operation in the case where i does not exceed the total number I (in the embodiment, I=4) of the warm-up tasks registered in the schedule table (No in step S116).

On the other hand, in the case where i exceeds I as a result of the increment in step S115 (Yes in step S116), the judgment result means the end of all tasks registered in the schedule table, including the analysis, and therefore, the process on the workstation 2 side returns to a point before step S101, and waits until a new task is registered in the schedule table.

By the way, the analyzing apparatus 1 having sent the analysis end notice signal to the workstation 2 in step S114, after a predetermined time has elapsed since then (Yes in step S117), transitions to the sleep state, that is, turns off the unit powers of all units of the analyzing section 30 (step S118). Specifically, the unit power controlling section 23 switches off the unit powers 31p, 321p, 322p, 323p and 324p of the units of the analyzing section 30 described above, and stops the electricity supply to the automatic sampler 31, the liquid sending pump 321, the injector 322, the column oven 323 and the detector 324. Then, the process on the analyzing apparatus 1 side returns to a point before step S106, and waits until the communicating section 60, which maintains the reception of electricity, receives the next warm-up start command signal from the workstation 2.

The above "predetermined time" as the judgment reference in step S117 may be arbitrarily set by the user, and may be 0 seconds, for example. Alternatively, this period may be several seconds to several minutes, and the electricity supply to the units may be maintained in the case where the operation acquiring section 21 detects a touch operation in a predetermined area on the touch panel 11 during the period. For example, the above predetermined area may be a GUI button displayed by the displaying section 40 and relevant to the operation control of the analyzing section 30.

As another example, for transitioning to the sleep state after the end of the analysis, a command may be given from the workstation 2. As an example, the command for transitioning to the sleep state may be incorporated at the end of the set of a plurality of the analyses respectively included in the batch files 512, 514, 516 and 518. In this case, instead of step S117 in FIG. 4, a command signal for transitioning to the sleep state is sent from the workstation 2 to the analyzing apparatus 1 (the illustration is omitted). A configuration in which the batch file includes the command for transitioning to the sleep state in this example may be adopted as the default operation mode of the above analysis controlling program. It is preferable that the user can arbitrarily change whether to enable the operation mode.

According to the present embodiment, the analyzing apparatus 1 turns off the unit powers of all units of the analyzing section 30 by the pressing of the energy-saving power switch 12 or the command from the workstation 2 so as to stop the electricity supply to all units (the transition to the sleep state). Thereby, the electricity consumption by the analyzing apparatus 1 is considerably reduced.

Further, according to the process described with reference to FIG. 4 and FIG. 5A, the unit powers of all units of the analyzing section 30 of the analyzing apparatus 1 in the sleep state are switched on, at the start time of the warm-up operation, which is created on the workstation 2 and registered in the schedule table, and thereby, the electricity supply to the all units is restarted (the cancel of the sleep state). Accordingly, the period during the units consume electricity is only the period during the analysis work including the warm-up operation and the execution of the analysis, resulting in a further contribution to the reduction in electricity consumption.

Furthermore, in the present embodiment, the communicating section 60 functions at all times, even while the analyzing apparatus 1 is in the sleep state, and therefore, can successively receive various control signals from the workstation 2. Based on them, the analyzing apparatus 1 can transition to the sleep state at an appropriate timing, and can automatically restart the analysis work at a timing desired by the user.

Here, a problem in that the command of the analysis execution is not given after the warm-up operation is completed in the analyzing apparatus 1 can occur due to a user's input error to the batch queue 510, or the like. In this case, in order to suppress unnecessary electricity consumption, a judgment step as to whether a predetermined time has elapsed may be provided between step S109 and step S111, and the analyzing apparatus 1 may be configured to transition to the sleep state again in the case where the command of the analysis start is not given for a very long time (for example, several tens of minutes to about one hour).

The example in which the four analysis works are intermittently executed has been described above. In addition to the example, the present invention can be applied to a case where "the user starts the analysis at night, goes home before the end of the analysis, and restarts the analysis immediately in the next morning", which is thought to be a more frequent use situation of the analyzing apparatus 1.

Figure 5B:
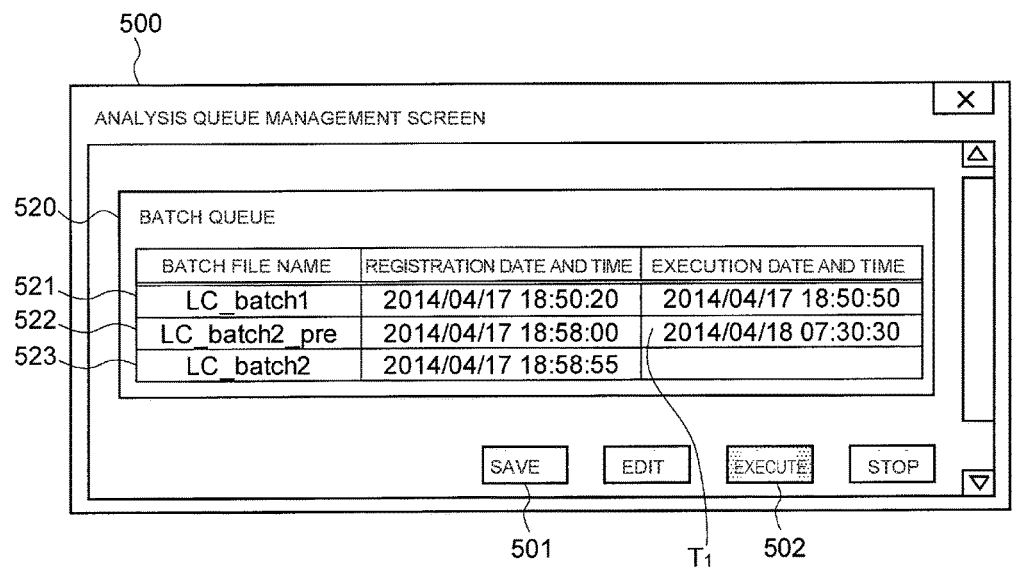

FIG. 5B shows another example of the schedule table edited on the analysis queue management screen 500. In a batch queue 520, three batch files 521 to 523 have been registered as tasks, and among them, the batch file 521 (LC_batch1) is already being executed.

The situation in the example will be described in more detail. The user started the analysis by the execution of the LC_batch1 before going home, wanted the warm-up operation to be completed shortly before the time when arriving at his or her laboratory in the next morning, and newly registered the batch file 522 relevant to the warm-up operation and the batch file 523 relevant to the execution of the analysis in the batch queue 520, in order. Here, for performing the exchange of the sample, the check of the state of the sample rack 310 and the like before starting the analysis in the next morning, the column "EXECUTION DATE AND TIME" for the batch file 523 is left blank, and the manual start by the user is scheduled. The value of the column "EXECUTION DATE AND TIME" for the batch file 521 that is already being executed is the time when the user manually commanded the start, which is automatically input afterward.

The above-described situation corresponds to a point between step S112 and step S113 in the flowchart shown in FIG. 4 (a connector A in FIG. 4). When the analysis relevant to the batch file 521 ends (Yes in S113), the analyzing apparatus 1 transitions to the sleep state (step S118), after the elapse of the predetermined time (Yes in S117). Then, at the execution date and time of the batch file 522 (the start time $T_1$ of the warm-up) (Yes in S105), the communicating section 60 receives the warm-up start command signal from the workstation 2 (step S106), and the warm-up operation in accordance with the batch file 522 is started (step S107). Then, after steps S108 to S109, the analysis controlling program waits for the analysis start command signal (step S111) from the workstation 2.

The present embodiment contributes also to the improvement of the reliability of the analysis result, in the following respect.

In the period from the reservation of analysis work to the start of the analysis work, the user as the operator of the analysis work is often absent around the analyzing apparatus 1 as in the case of the above example, and another user mistakenly (or a malicious third person intentionally) operates the unit in the period which affects the analysis result adversely, in some cases. According to the present embodiment, the unit powers of all units of the analyzing apparatus 1 are turned off when the analysis is not executed, and thereby, it is possible to decrease the probability of the occurrence of an interventional act with intention or negligence by a third person.

Processing Flow by Sample Analyzing System:
Second Example

Figure 6:
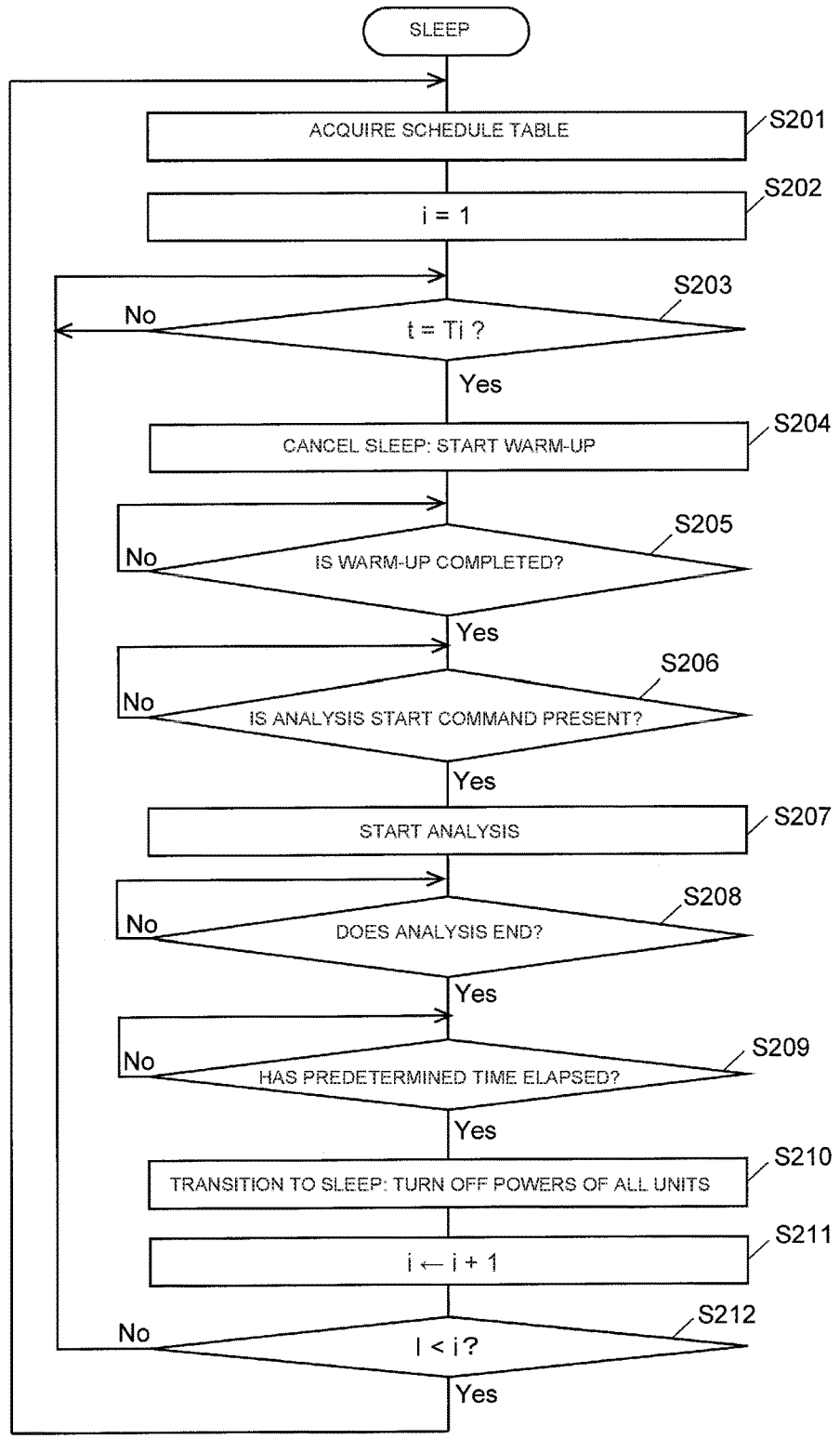
FIG. 6 is a flowchart showing another example of the flow of a process by the analyzing apparatus when the sample analyzing system shown in FIG. 1 performs the analysis work.

As a modification of the process described with reference to FIG. 4, the analyzing apparatus 1 may store and refer to the schedule table. FIG. 6 is a flowchart showing another example of the processing flow by the analyzing apparatus 1 in the sample analyzing system.

First, the communicating section 60 acquires the schedule table from the workstation 2 (step S201). For example, the batch queue 510 shown in FIG. 5A is acquired. In the batch queue 510, the processes of steps S101 to S103 are completed on the workstation 2 side.

The processes in steps S202 to S212 are the same as those in S104, S105, S107, S108, S110, S112, S113, S117, S118, S115 and S116 shown in FIG. 4, respectively. Among them, with respect to the processes performed on the workstation 2 side in FIG. 4, the analysis controlling section 22 of the analyzing apparatus 1 may perform these processes, instead of the analysis controlling program installed in the workstation 2. Similarly to the above first example, a judgment step as to whether a predetermined time has elapsed may be provided between step S205 and step S206.

Modification

The present invention is not limited to the above-described embodiments, and may be appropriately modified in the scope of the spirit of the present invention.

For example, although it has been described that the start times $T_i$ of the warm-up operation are independently designated in the above embodiments, the time point when the execution button 502 is clicked on the analysis queue management screen 500 (see FIG. 5) or the time point when a predetermined time has elapsed since the end of the preceding analysis may be adopted as the next $T_i$.

Furthermore, although the configuration has been described in which only the unit powers are turned off in the sleep state of the analyzing apparatus 1, the electricity consumption can be further reduced by a configuration of turning off also the controlling-section power 20$p$ and the power circuits uniquely included in the touch panel 11, the energy-saving power switch 12, the displaying section 40 and the storage section 50 respectively. In the case where the controlling-section power 20$p$ is turned off in the sleep state, the communicating section 60 may be configured to turn on the controlling-section power 20$p$, as a trigger, when the communicating section 60 receives the control signal from the workstation 2.

Further, although the configuration has been described in which the unit power controlling section 23 collectively stop/restarts the electricity supply to all units of the analyzing section 30 in the above embodiment, some of all units may be selectively switched or each unit may be switched at individual timings with respect to ON/OFF of the unit power.

As a further modification, although the system controller 110 has been described as the controlling apparatus in the present invention, the same function may be implemented by installing a predetermined program in a controlling computer provided separately from the analyzing apparatus 1.

In addition, the touch panel is not an essential component in the analyzing apparatus according to the present invention, and therefore, the touch panel 11 can be excluded in the analyzing apparatus 1. In this case, the operation acquiring section 21, which is means for specifying the touch position coordinates, can be also excluded.

The units described in the above embodiments are merely a part of examples, even in the case where the analyzing apparatus is a LC, and it is natural that the unit in the present invention can adopt various forms depending on the type and configuration of the apparatus. That is, the unit in the present invention may be any functional unit as a machine element that relates to analysis work including a plurality of steps and that consumes electricity in the execution of the steps.

REFERENCE SIGNS LIST

1 . . . Analyzing Apparatus
10 . . . Main Power Switch
11 . . . Touch Panel
110 . . . System Controller
12 . . . Energy-Saving Power Switch
2 . . . Workstation
20 . . . Controlling Section
20p . . . Controlling-Section Power
21 . . . Operation Acquiring Section
22 . . . Analysis Controlling Section
23 . . . Unit Power Controlling Section
24 . . . Analysis Result Acquiring Section
30 . . . Analyzing Section
31 . . . Automatic Sampler
310 . . . Sample Rack
311 . . . Check Window
31p, 321p, 322p, 323p, 324p . . . Unit Power
32 . . . LC Section
321 . . . Liquid sending Pump
322 . . . Injector
323 . . . Column Oven
324 . . . Detector
40 . . . Displaying Section
50 . . . Storage Section
510, 520 . . . Batch Queue
511, 512, 513, 514, 515, 516, 517, 518, 519, 521, 522, 523 . . . Batch File
60 . . . Communicating Section
60p . . . Communicating-Section Power
$T_1, T_2, T_3, T_4$ . . . Start Time of Warm-Up Operation

The invention claimed is:

1. A controlling apparatus for an analyzing apparatus, the controlling apparatus controlling an operation of the analyzing apparatus and making the analyzing apparatus execute a predetermined analysis, the controlling apparatus comprising:

a) a communicating module that maintains reception of electricity when the analyzing apparatus is in a power-on state, and is capable of receiving a control signal from an external apparatus at all times when the analyzing apparatus is in the power-on state; and b) unit power controlling means configured to acquire the control signal through the communicating module, stop electricity supply to a unit of the analyzing apparatus at a first timing based on the control signal, and restart the electricity supply to the unit at a second timing based on the control signal, wherein the second timing is a time point when the communicating module receives a signal, as the control signal, the signal being for commanding a start of analysis work registered in an analysis schedule that is managed by the controlling apparatus or the external apparatus.

2. The controlling apparatus according to claim 1, wherein the unit power controlling means stops the electricity supply to all of a plurality of units of the analyzing apparatus at the first timing, and restarts the electricity supply to all of the plurality of units at the second timing.

3. A non-transitory computer readable media recording a controlling program configured to make a computer function as the unit power controlling means of the controlling apparatus according to claim 2.

4. A non-transitory computer readable media recording a controlling program configured to make a computer function as the unit power controlling means of the controlling apparatus according to claim 1.

5. An analyzing system comprising:
the controlling apparatus of claim 1; and
the external apparatus, wherein
the external apparatus is configured to manage the analysis schedule, and is further configured to send the signal, as the control signal, in response to a present time being a time registered in the analysis schedule to start the analysis work.

6. The controlling apparatus according to claim 1, wherein
in a case where the electricity supply to the unit is stopped and the analysis work is finished, the unit power controlling means is configured to automatically restart the electricity supply to the unit at a third timing based on the control signal, and
the third timing is a time point when the communicating module receives an additional signal, as the control signal, the additional signal being for commanding a start of an additional analysis work registered in the analysis schedule that is managed by the controlling apparatus or the external apparatus.

7. The controlling apparatus according to claim 1, wherein
the unit power controlling means is configured to restart the electricity supply to the unit at the second timing based on the control signal, such that the analyzing apparatus performs a warm up operation.

* * * * *